(12) United States Patent
Owens et al.

(10) Patent No.: US 7,938,008 B2
(45) Date of Patent: May 10, 2011

(54) NON-DESTRUCTIVE EXAMINATION APPARATUS AND METHOD FOR GUIDED WAVES

(75) Inventors: Steven E. Owens, Bellefonte, PA (US); Joseph L. Rose, State College, PA (US); Roger L. Royer, Jr., Williamsburg, PA (US)

(73) Assignee: FBS, Inc., State College, PA (US)

( * ) Notice: Subject to any disclaimer, the term of this patent is extended or adjusted under 35 U.S.C. 154(b) by 577 days.

(21) Appl. No.: 11/946,281

(22) Filed: Nov. 28, 2007

(65) Prior Publication Data

US 2008/0127732 A1 Jun. 5, 2008

Related U.S. Application Data

(60) Provisional application No. 60/867,468, filed on Nov. 28, 2006.

(51) Int. Cl.
*G01N 29/00* (2006.01)

(52) U.S. Cl. ............... 73/632; 73/599; 73/602; 73/634; 73/642

(58) Field of Classification Search ............ 73/632, 73/624, 625, 633, 536, 639, 640, 641, 642, 73/599, 602, 634
See application file for complete search history.

(56) References Cited

U.S. PATENT DOCUMENTS

| | | | | | |
|---|---|---|---|---|---|
| 2,779,880 | A | * | 1/1957 | Malherbe | 310/335 |
| 3,925,692 | A | * | 12/1975 | Leschek et al. | 310/327 |
| 4,481,822 | A | * | 11/1984 | Kubota et al. | 73/625 |
| 4,495,817 | A | * | 1/1985 | Hunt et al. | 73/624 |
| 4,567,048 | A | * | 1/1986 | Gruetzmacher | 426/250 |
| 4,755,975 | A | * | 7/1988 | Ito et al. | 367/140 |
| 5,974,888 | A | * | 11/1999 | Bonitz | 73/624 |
| 5,992,235 | A | * | 11/1999 | Fischer et al. | 73/617 |
| 6,360,609 | B1 | * | 3/2002 | Wooh | 73/602 |
| 6,799,466 | B2 | * | 10/2004 | Chinn | 73/622 |
| 7,389,694 | B1 | * | 6/2008 | Hay et al. | 73/635 |
| 2004/0093949 | A1 | * | 5/2004 | Alleyne | 73/625 |
| 2007/0051177 | A1 | * | 3/2007 | Gifford et al. | 73/620 |
| 2008/0229834 | A1 | * | 9/2008 | Bossi et al. | 73/627 |

* cited by examiner

*Primary Examiner* — Jacques M Saint Surin
(74) *Attorney, Agent, or Firm* — Duane Morris LLP

(57) ABSTRACT

A method of performing a non-destructive examination of a piece of material, having the steps of providing an angle beam wedge and at least two transducers placed upon the wedge, wherein the transducers are placed in a phased array, placing the wedge upon the piece of material to be examined, producing a guided wave into the piece of material to be examined, wherein the guided wave is placed into the material through a synthetically changed incident angle, receiving the guided wave from the piece of material, and determining one of a presence of defects and lack of defects in the piece of material from the received guided wave. Transducers used may include 360 degree guided wave, radial polarized units, parallel shear units for shear horizontal activation and guided wave wheel probes.

12 Claims, 15 Drawing Sheets

NON-DESTRUCTIVE EXAMINATION APPARATUS AND METHOD FOR GUIDED WAVES

The present application claims priority under 35 U.S.C. §119(e) to U.S. Provisional Patent Application 60/867,468 filed on Nov. 28, 2006, the entirety of which is incorporated by reference herein.

FIELD OF THE INVENTION

The present invention relates to non-destructive examination and structural health monitoring. More specifically, aspects of the present invention relate to conducting non-destructive examination and/or structural health monitoring of materials through producing guided waves in the materials under examination.

BACKGROUND INFORMATION

Ultrasonic non-destructive examination and structural health monitoring of materials produces many challenges for individuals involved with the examination or monitoring. Two types of inspection conducted on materials include bulk wave investigation and guided wave investigation. Each of the investigation techniques has its own advantages and disadvantages.

Guided wave investigation, in particular, evaluates materials by exposing those materials to guided waves, waves that propagate internally between or along boundaries; however, conventional systems and methods employed to produce guided waves have significant shortcomings. Unique dispersion curves can be calculated for every structure of interest. Dispersion curves exemplify all of the mode possibilities in that structure. Each point on the curve exhibits different displacement characteristics that may be utilized for different inspection needs. It is desirable to design special sensors that are capable of efficiently exciting different regions on these curves curve. It would also be advantageous to have special sensors that are capable of exciting multiple locations or sweeping throughout the dispersion curve space to take advantage of the characteristics of multiple locations on the curve.

There is a need to provide a method for introducing a guided wave into a material, such as a rail, as the sensor is moved along the structure.

There is a further need to provide a method and apparatus to allow for changing the effective incidence angle of guided waves as they are inserted into material to be evaluated, thereby exciting multiple modes and allowing scanning throughout the volume of the structure. There is a further need to provide specialized sensors for structural health monitoring, which are capable of exciting dominant shear horizontal displacement. Shear horizontal displacements are desired for numerous reasons. For example, shear horizontal waves are less affected by liquid loadings than conventional longitudinal guided waves. Also, shear horizontal waves, in some cases, can provide increased penetration power and improved damage detection sensitivity.

There is also a need to provide a method and apparatus for investigation of rail heads, which minimizes the need for bulk wave investigation and instead uses guided waves for inspection, thereby overcoming the deficiencies of bulk wave investigations.

There is a further need to provide a guided wave inspection technique that will investigate rail heads, webs, and bases and prevent anomalies obtained during non-destructive examination from field factors such as rail shelling. Additionally, it may be advantageous to have a sensor that is used to detect shelling.

SUMMARY OF THE INVENTION

It is therefore an objective of an aspect of the invention to provide a method for performing efficient guided wave non-destructive examination of material pieces in a cost effective and accurate manner.

It is also an objective of the invention to provide a method and apparatus to allow for synthetic manipulation of the incident angle of guided waves as they are inserted into material to be evaluated, thereby allowing scanning of the volume through the utilization of different and/or multiple modes.

It is also an objective of an aspect of the invention to provide a method of generating guided waves in material without requisite expensive and time consuming set up for conventional guided wave technologies and systems.

It is a further objective of the invention to provide a method and apparatus for investigation of rail heads, which minimizes the need for bulk wave investigation systems and instead uses guided waves for inspection. It is a still further objective of the invention to provide a guided wave inspection technique that will investigate rail webs, heads, and bases and prevent anomalies obtained during bulk wave investigations such as, for example, from rail shelling. Additionally, it may be an objective to have a sensor that is used to detect shelling.

The objectives of the inventions are achieved as illustrated and described. An exemplary embodiment of the present invention provides a method of performing a-non-destructive examination or structural health monitoring of a piece of material, comprising providing an angle beam wedge and at least two transducers placed upon the wedge, wherein the transducers are placed in a phased array, placing the wedge upon the piece of material to be examined, producing a guided wave into the piece of material to be examined, wherein the guided wave is placed into the material through a synthetically changed incident angle, receiving the guided wave from the piece of material, and determining one of a presence of defects and lack of defects in the piece of material from the received guided wave.

In a further exemplary embodiment of the invention, the method is provided as above and further comprising the step of controlling a mode of the produced guided wave by changing a time delay schedule across the array followed by changing an excitation frequency after producing the guided wave in the piece of material.

In another exemplary embodiment of the invention, the method may further comprise selecting a wave structure for the wave prior to producing the guided wave, and selecting a frequency of the guided wave prior to producing the guided wave.

In a still further exemplary embodiment of the invention, the non-destructive examination or structural health monitoring sensor has a housing made of a polymer or metallic material. The piezo element may be segmented along the length or radially.

In another exemplary embodiment of the invention, a method of performing a non-destructive examination of a piece of material is provided. The method comprises providing a non-destructive examination or structural health monitoring sensor having a polymer or metallic housing and a piezo element placed at least partially within the polymer housing, wherein the piezo element is at least two truncated frustoconical shapes, placing the sensor on the piece of material, exciting the sensor at an angle between 0° and 360° over the material to produce a guided wave in the material, receiving the guided wave from the piece of material; and determining a presence of defects in the material from the received guided waves. The sensor may be segmented. Additionally, a frequency may be changed during the producing of the guided wave in the material. The incident angle of the sensor is selected, based on dispersion curve characteristics. The sensor is a 360° or less angle beam wedge transducer.

The present invention also provides for an arrangement for analysis of defects in a piece of material, comprising a body in a shape of one of a disk and a ring, the body made of a polarized material, wherein the polarized material is polarized in a direction from a center of the one of the disk and the ring to an outside circumferential edge of the one of the disk and the ring. The sensor is a radially polarized disk for the purpose of structural health monitoring. Also, the sensor could be a parallel shear polarized bar for the purpose of structural health monitoring, whereby the advantage of the sensor is the ability to introduce dominant shear horizontal energy into the structure.

DETAILED DESCRIPTION

Aspects of the present invention provide for utilization of bulk wave devices and non-standard angle beam devices to create guided wave devices. In an aspect of the present invention, these guided wave devices allow for input of guided waves into materials to be evaluated. The methods and apparatus of aspects of the invention allow for accurate monitoring of these materials for defects. By providing a designer with better tools to select excitation regions within and move throughout the dispersion curve space and also to have better mode control with respect to exciting only a particular mode. By careful modification of sensor angle and frequency upon the materials, it becomes possible to create special devices that will input guided waves into material shapes such as plate, pipe and rail, as non-limiting examples.

Aspects of the invention also provide for selection of design criteria for sensor angles and sensor array time delay schedules, along with design selection of an appropriate lower frequency sensor compared to ordinary bulk wave sensors. Bulk wave devices that may be used to produce guided wave systems include normal beam transducers, fixed angle, angle beam probe on Plexiglas (or other material) wedge, variable angle beam probes, comb arrays, comb arrays on a Plexiglas wedge, whereby time delay profiling can produce any desired entry angle into a structure and couplant filled rail inspection wheels with transducers designed for guided wave excitation.

Figure 1:
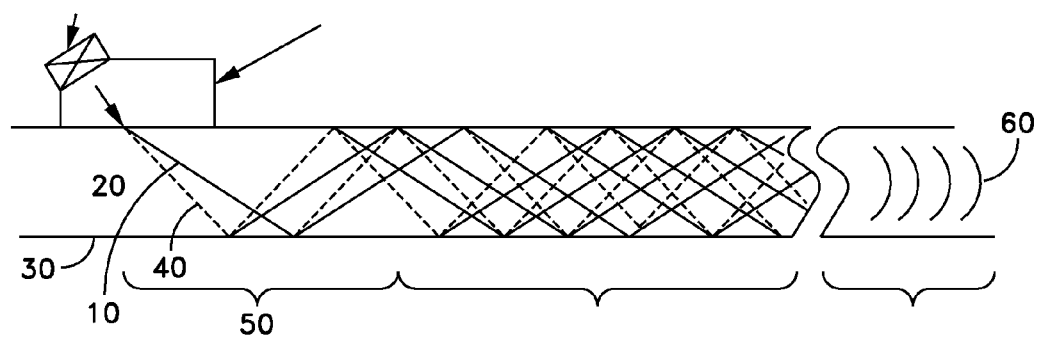
FIG. 1 is a traditional development of a guided wave in a piece of material through angle beam excitation.

The probes presented above are modified to steer ultrasonic beams to a desired position or entry angle inside a structure. The ultrasonic beam placed into the material refracts and bounces back and forth until a wavefront develops. Referring to FIG. 1, a longitudinal wave 10 is inserted into the material 20 and reflect off of the bottom surface 30 of the material 20. In addition to the longitudinal wave 10, a shear wave 40 may be inserted into the traditional bulk wave region 50 to again allow the wave to reflect internally off of the bottom surface 30 in the material 20. The longitudinal wave 10 and the shear wave 40 reflect numerous times within the material 20 until a wavefront develops. As a result of the numerous waves propagating through the material, superposition of the waves may occur. A guided wave, 60 is thereby created within the material 20 that propagates along the length of the material. The guided wave may then encounter a defect, which will cause a portion of the energy to be reflected. Both the reflected and transmitted portions of the energy can then be received and analyzed.

Figure 2:
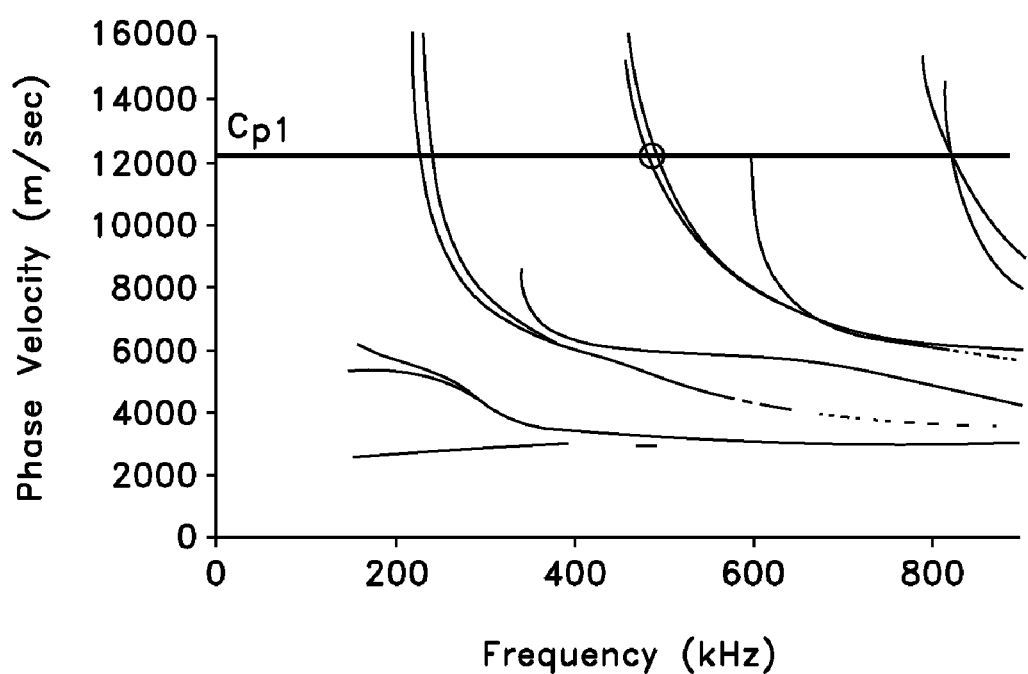
FIG. 2 is a phase velocity dispersion curve, which is used to select modes and frequencies for excitation. An activation line for a specific excitation angle is shown on the curve.

An aspect of the invention provides for the methods and systems to create guided waves to fill all or a portion of an entire volume of a structure and then propagate these waves over long distances by using special wave structure characteristics that remain similar as the wave propagates. The wave structure, the distribution across the structure of various displacement and stress patterns, that relates to sensitivity to certain defects found across the thickness of the structure, can be controlled by changing sensor impingement angle or time delay profiles, and frequency. Longer wavelengths and appropriate entry angles makes guided wave propagation possible. The selection of frequency and angle is based on selection of mode and frequency from a phase velocity dispersion cure as illustrated in FIG. 2. A sensor is then designed to activate the respective mode accordingly. The sensor may also be modified to activate other modes accordingly.

Referring to FIG. 2, a phase velocity dispersion curve is illustrated. In the vertical axis, the phase velocity in (m/sec) is presented. In the horizontal axis, the frequency in kilohertz is provided. The angle chosen for impartation of the ultrasonic beam is based on Snell's law, where $\theta = \sin^{-1}(C_1/C_p)$ where $C_p$ is on the phase velocity dispersion curve of FIG. 2 and $C_1$ is the longitudinal wave velocity in the wedge or fluid considered to transport the ultrasonic energy from the sensor to the test structure.

Figure 3:
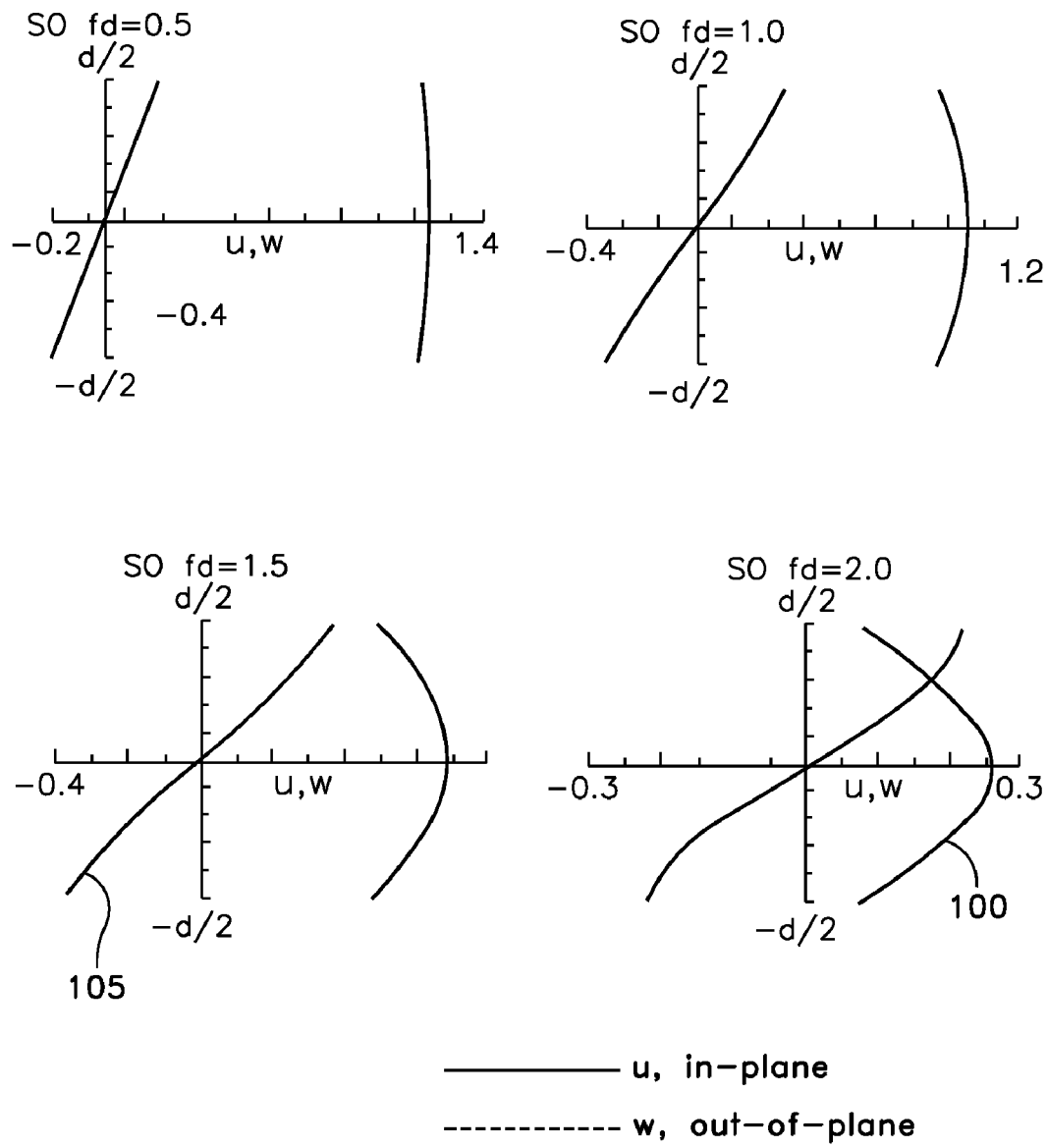
FIG. 3 is a wave structure profile for various fd values for S0 mode. The wave structure profiles show how the in-plane and out-of-plane energy distributions vary throughout the thickness of the structure.

The value $C_{p1}$ can be selected anywhere along the $C_p$ axis based on desired ultrasonic guided wave performance. Frequency may also be selected anywhere along the horizontal axis that achieves the desired wave structure. As an example, FIG. 3 illustrates wave structure profiles at various fd values for an S0 mode, and illustrates how in-plane and out-of-plane wave structure profiles vary as a function of frequency thickness product. The value of u is for in-plane wave structure profiles 100 and the value of w 105 is for out-of-plane wave structure profiles. The wave structure profiles may be chosen, for example, to limit the amount of leakage of ultrasonic energy into a surrounding fluid, based upon the geometric characteristics of the materials.

Figure 4:
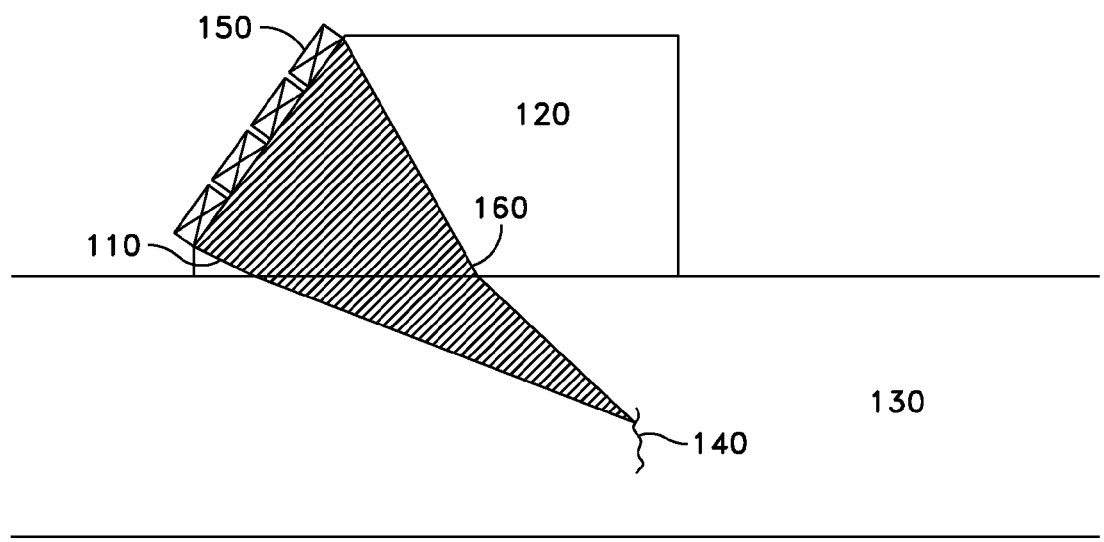
FIG. 4 is an example of one way conventional phased array angle beam wedges are used to perform bulk wave inspections.

Referring to FIG. 4, a conventional angle beam wedge 120 is placed upon a block of material 130. The angle beam wedge 120 allows for impartation of ultrasonic energy in wave form 160 into a material to be evaluated 130. The material to be evaluated 130 may have, in the illustrated embodiment, a defect 140. The placement of the angle beam wedge 120 and the angle at which the transducers 150 are to the material to be evaluated 130 causes the ultrasonic beam to enter the material to be evaluated 130 and show the flaw. The impartation of the ultrasonic beam 160, however, does not result in a guided wave for the material. Thus, if the defect were not directly within the pattern of the bulk wave, the defect would not have been detected. The transducers 150 are phased with time delays to move the focal point around within the material 130.

Figure 5:
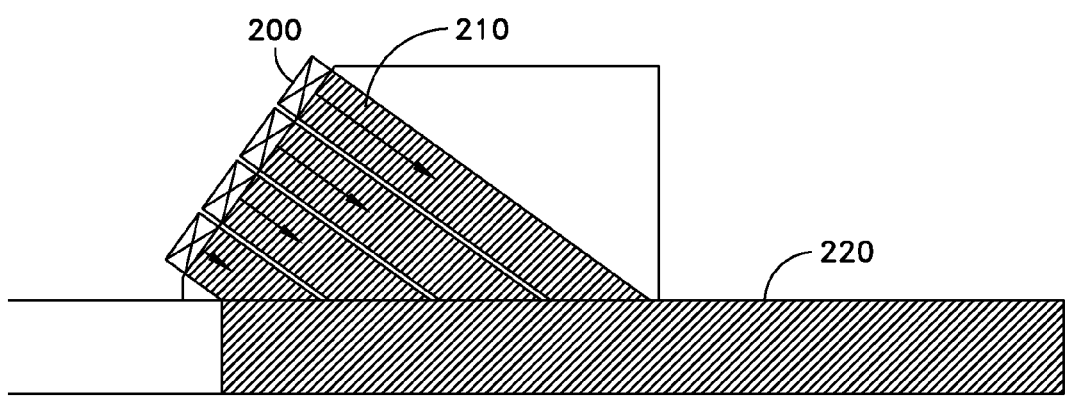
FIG. 5 is a guided wave phase array angle beam probe.

Referring to FIG. 5, an alternate time delay schedule for phasing can be used to synthetically change the incident angle of the wedge, and thereby sweep through the dispersion curve space. Transducers 200 are located on a block of material 210 that are placed on a material to be evaluated 220. The individual transducers 200 are placed on an angle beam wedge in the illustrated embodiment. In the illustrated embodiment, four transducers 200 are positioned on the angle beam wedge, however any number of transducers 200 greater than one may be used. The placement of the transducers 200 is in a form of a phased array. A guided wave of ultrasonic energy is then input into the piece of material to be examined 220 by activating the transducers 200, wherein the guided wave is placed into the material 220 through a synthetically changed incident angle. The synthetically changed incident angle is produced by controlling a mode by changing a time delay schedule across the array of transducers 200. An excitation frequency may also be changed during production of the guided wave in the piece of material to be evaluated 220. The produced guided wave extends through the piece of material to be evaluated and then is received at the same sensor, or a different sensor. A presence or lack of presence of defects in the piece of material is then determined from the received wave.

Figure 6:
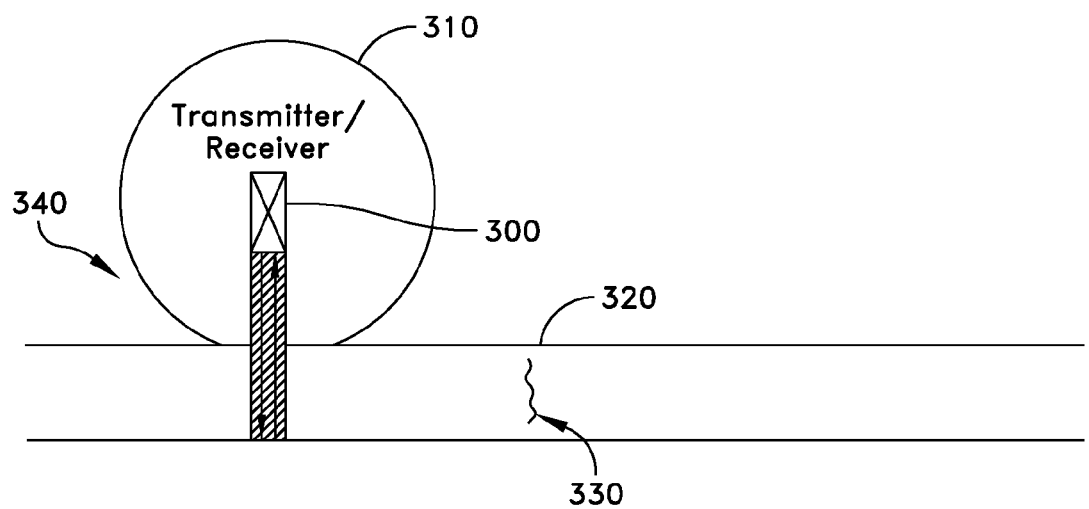
FIG. 6 is a conventional bulk wave wheel probe. Transducers may also be used at an incident angle, but information is not used to inspect beyond the region under the wheel, or within the region where a guided wave would develop. The excitation angles are not determined, based on a dispersion curve.

Referring to FIG. 6, a conventional bulk wave wheel probe 340 is illustrated. A combined transmitter/receiver 300 is positioned in a wheel 310. The wheel 310 is rolled over a rail 320. Material defects 330 in the rail 320 are only found by rolling the bulk wave wheel probe 340 over the defect 330 when bulk waves are input into the rail 320. Defects that are totally vertical in nature, however, cannot be detected through use of the conventional bulk wave wheel probe 340. Defects in the portion of the base not directly under the web of the rail are missed. Defects under shelling are also missed.

Figure 7:
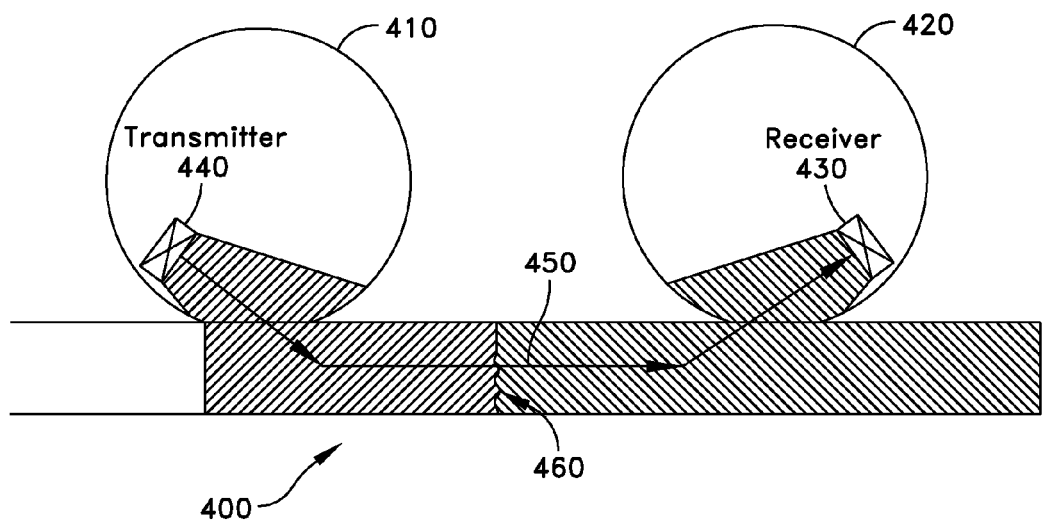
FIG. 7 is a through transmission guided wave wheel for investigating rail.
Figure 8:
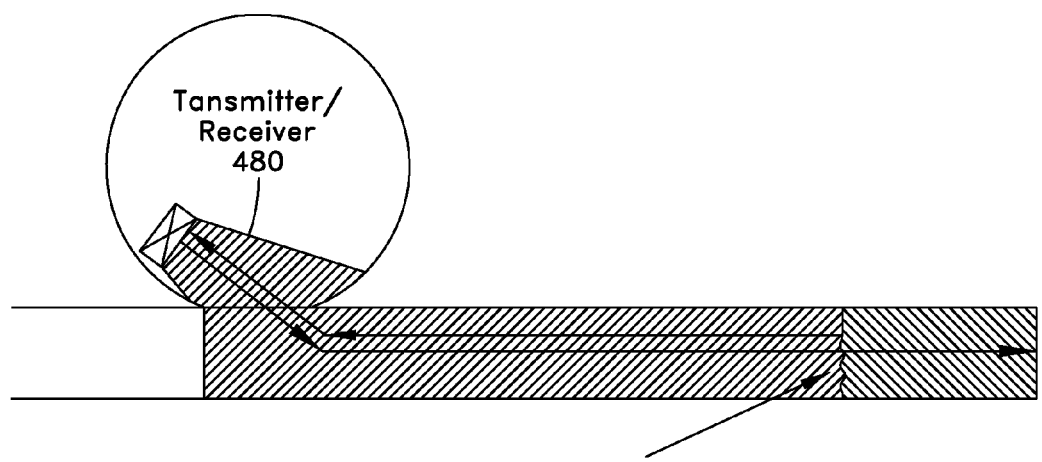
FIG. 8 is a pulse echo guided wave wheel for investigating rail.

Referring to FIG. 7, a through transmission guided wave wheel arrangement is provided that is used for rail inspection. The through transmission guided wave wheel 400 is presented as a first wheel 410 and a second wheel 420. A transmitter 440 is located in the first wheel 410 and a receiver 430 is located in the second wheel 420. To conduct the investigation, the transmitter 440 is located in the first wheel 410 and is angled such that ultrasonic waves from the transmitter 440 enter the rail 450 and propagate down the rail 450 to the second wheel 420 and the receiver 430 located within. In the illustrated exemplary embodiment, a transverse defect 460 is detected through the guided waves traveling down the rail when the receiver 430 detects the guided waves traveling in the rail 450. Referring to FIG. 8, the guided wave wheel arrangement may also be configured such that the transmitter/receiver 480 is located within one wheel. Defects are detected through analysis of guided wave signals wherein a specific mode may be selected to inspect for head defects, base defects, shelling, weld inspection, or bolt hole cracks.

Figure 9:
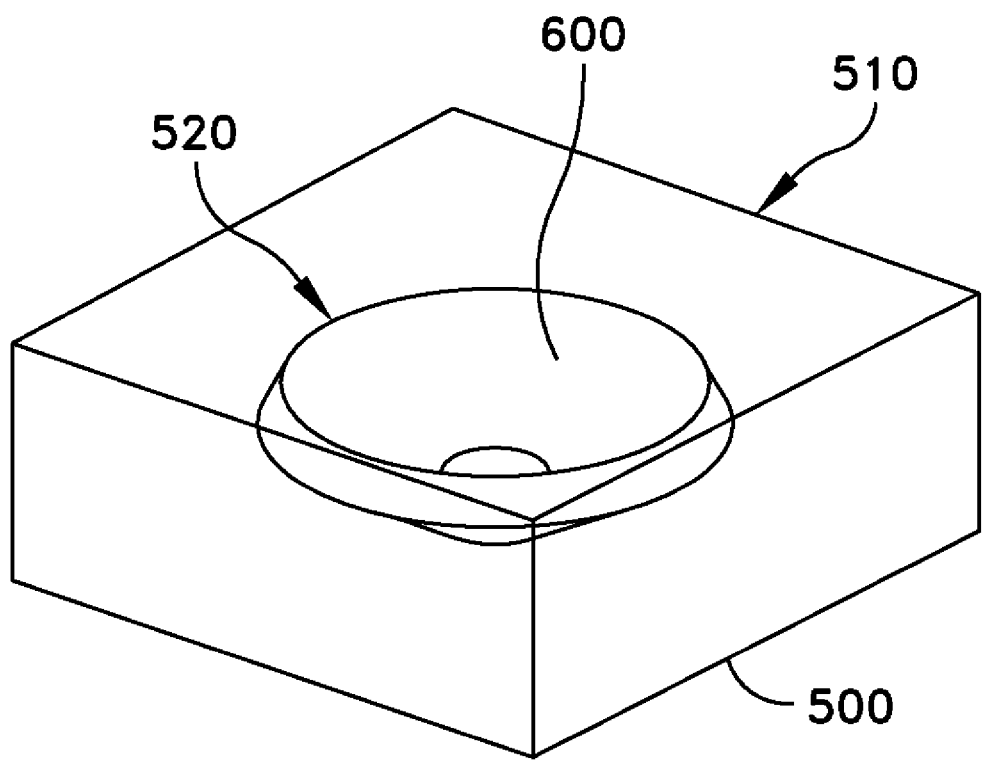
FIG. 9 is a isometric view of a 360° angle beam sensor for guided wave applications.

Referring to FIG. 9, an isometric view of a 360° piezoelectric sensor used, for example, to evaluate a plate is presented. Structural health monitoring or nondestructive testing, more specifically ultrasonic tomography are applicable applications. A piezoelectric sensor 500 comprises a non-destructive examination sensor, having a housing 510, and a piezo element 520 placed at least partially within the housing 510, wherein the piezo element 520 is a combination of two frustoconical shapes for production of a guided wave. The sensor 500 is constructed such that the sensor 500 may be placed upon a piece of material, such as a flat plate, and ultrasonic energy imparted into the plate in a 360° radius. An advantage for this configuration is the ability to have mode control. This makes signal processing easier and opens up more possibilities for signal processing. This configuration allows for selecting certain modes for detection reasons; such as for seeing surface or subsurface defects, or increasing evaluation sensitivity due to liquid loading.

Figure 10:
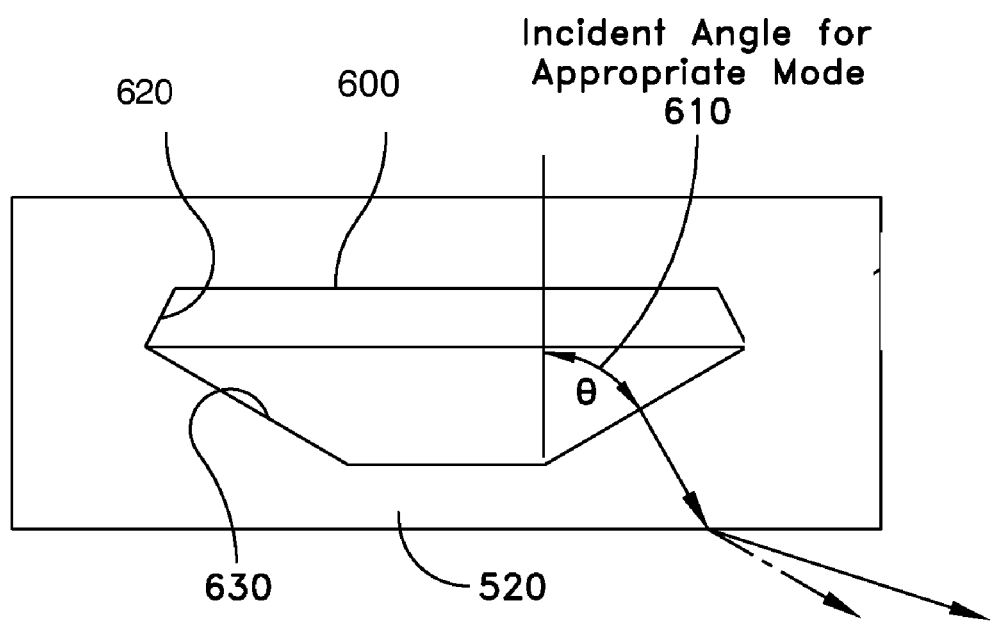
FIG. 10 is a side view of the 360° sensor for guided wave applications, showing the incident angle.
Figure 11:
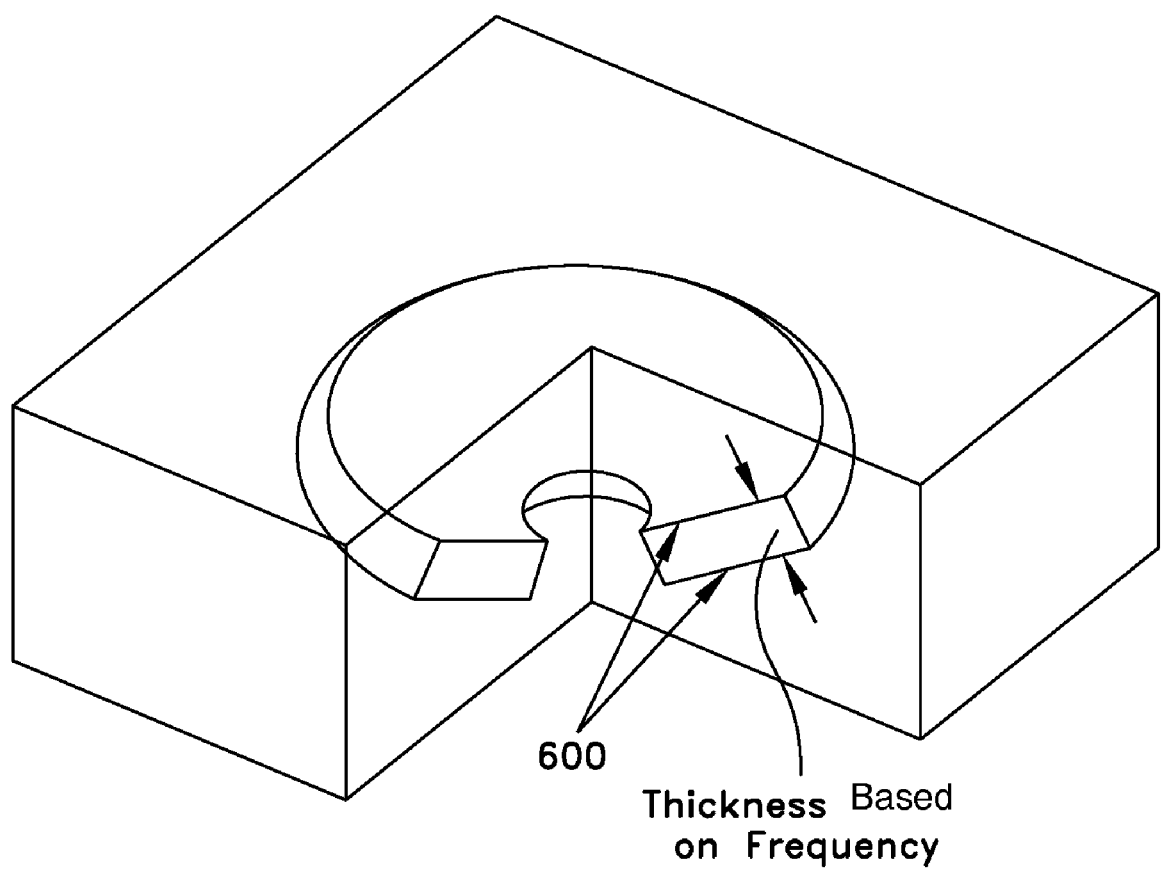
FIG. 11 is an isometric cut away view of the 360° sensor for guided wave applications.

Referring to FIGS. 10 and 11 respectively, a side view of the 360° sensor of FIG. 9 is illustrated and a isometric cut away view of the 360° sensor is provided. The 360° sensor is designed to have a thickness 600 based on a frequency desired for excitation as well as an incident angle 610 that allows for an incident angle for a desired mode. The thickness of the swept profile is based on the excitation frequency desired and the incident angle is calculated by using Snell's law for the appropriate refracted angle in the structure to be excited. Through this configuration, different incident angles and frequencies at any location on the dispersion curve can be selected. The sensor 500 may also be segmented and used with a phased array system, if desired. The sensor may also be configured in a flipped configuration, where the configuration focuses sound energy to a central point. The housing 510 may be made of any polymer or metallic material, such as Plexiglas as a non-limiting example, for housing the piezo element 520. The piezo element 520, as provided in FIG. 10 has a first truncated cone shape 620 and a second top portion that is also a truncated cone shape 630. Other configurations are also possible and therefore the illustrated embodiment is merely exemplary.

Figure 12:
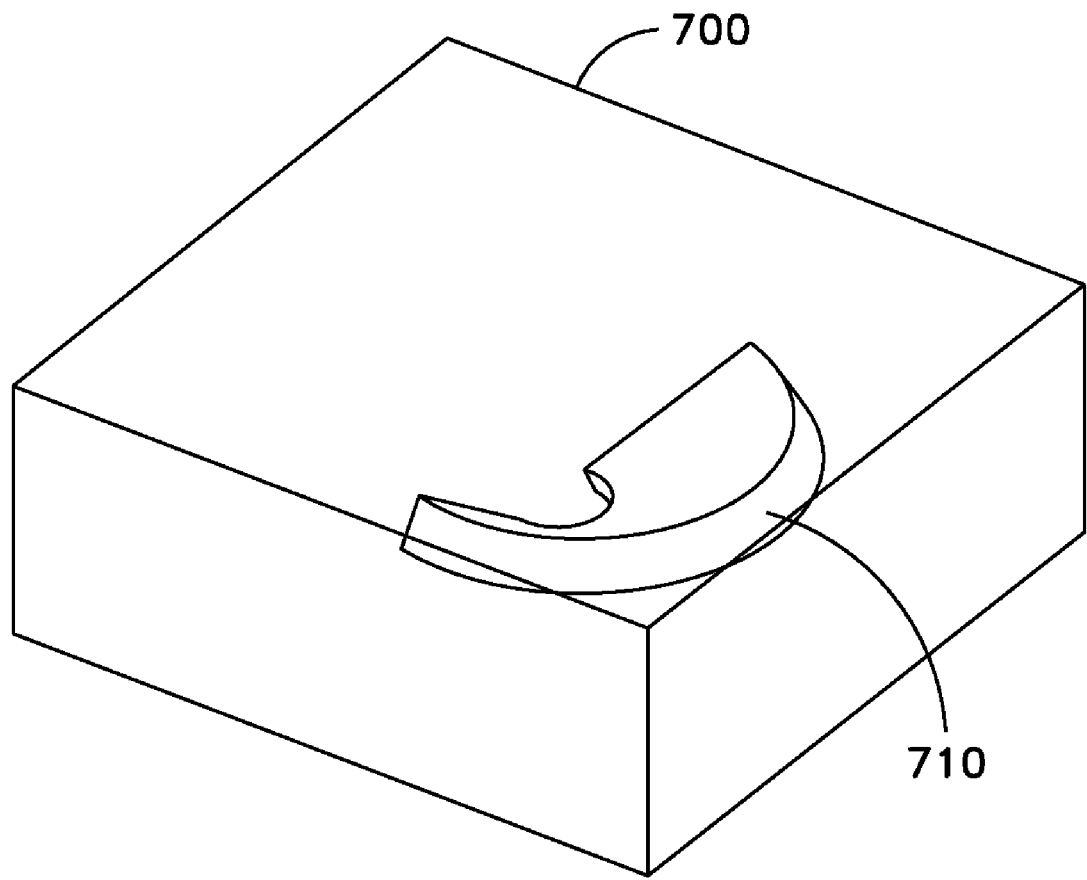
FIG. 12 is an isometric view of a 180° sensor for guided wave applications.

Referring to FIG. 12, an isometric view of a 180° sensor is provided. The construction of the 180° sensor is similar to that of the 360° sensor. The 180° sensor has a housing 700 that is made of a polymer or metallic material. A piezo element 710 is constructed in a 180° sensor arrangement, essentially half of the piezo element of FIG. 11. Any specific amount of piezo element 710 may be created as desired. As in the 360° sensor, the 180° sensor may be segmented.

Figure 13:
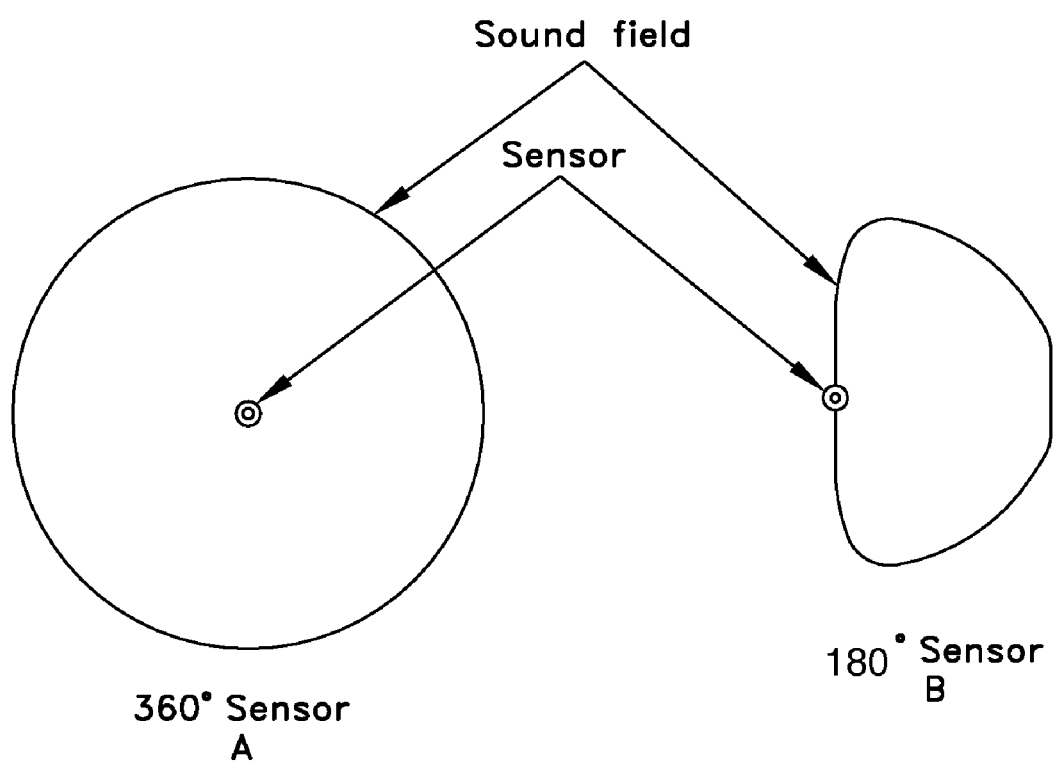
FIGS. 13A and 13B are sound fields for sensors for guided wave applications for a 360° and a 180° arrangement.

Referring to FIGS. 13A and 13B, representative ultrasound fields of the sensors of FIGS. 9 and 12 are provided. In FIG. 13A, the sensor of FIG. 9 has an illustrated sound field of 360°. In FIG. 13B, the sensor of FIG. 12 has a 180° sound field.

Figure 14:
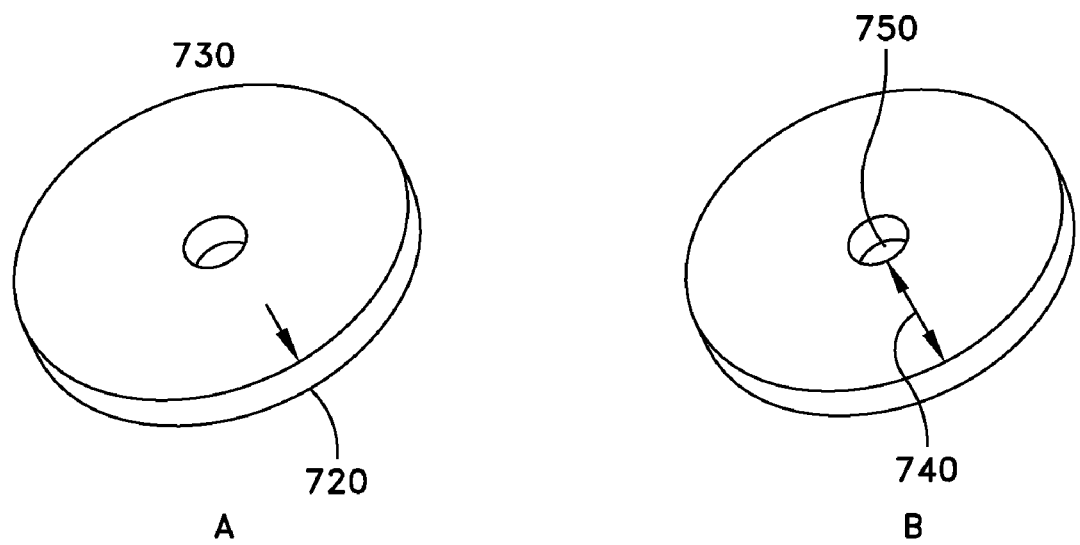
FIGS. 14A and 14B are standard ring polarization and radial ring polarization transducers for guided wave excitation.

Referring to FIGS. 14A and 14B, ring sensors for structural health monitoring or guided wave non-destructive examination are illustrated. In FIG. 14A, a standardized/conventional polarization is presented where the polarization is conducted through the thickness 720 of the ring 730. When a standardized/conventional polarization is chosen, a weak radial mode is also excited. In an exemplary embodiment of the invention, polarization may be performed through the ring 750 in a radial direction 740. The polarization of the ring 750 in the radial direction 740 allows for the polarization of the element to be in the direction that primary displacement is desired, to potentially achieve more efficient radial excitation. The natural frequency of the sensor may be changed, in this exemplary embodiment, by changing the radius of the disk.

Figure 15:
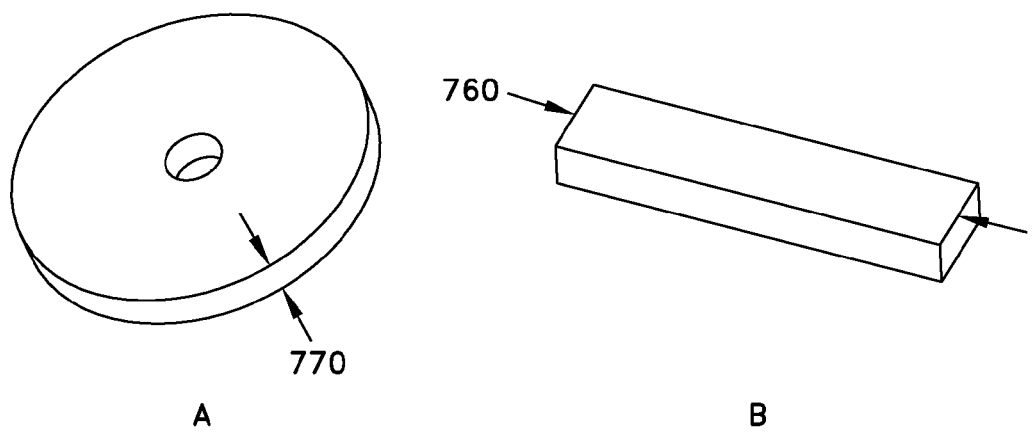
FIGS. 15A and 15B illustrate a standard disk polarization and a parallel shear polarization for guided wave excitation.

Referring to FIGS. 15A and 15B, a conventional polarization and a parallel shear polarization are presented. The sensors provided in these figures may be used, for example, in structural health monitoring systems. As provided in FIG. 15A, a traditional guided wave structural health monitoring sensor 760 is illustrated that is polarized through the thickness of the disk 770. Referring to FIG. 15B, a parallel shear polarization is presented for the excitation of shear horizontal waves. By utilizing shear horizontal waves, these waves are less sensitive to surface conditions, such as water loading and coatings. For example, using parallel shear polarization, sensors may be utilized on wet aircraft wings where conventional sensors, as provided in FIG. 15A, would provide a signal that contains significantly more noise, to the point that detection of defects is no longer possible, or only that larger defects are detectable. Images can be created from the data collected when energy is sent between two or more of the sensors. The image may be created by extracting features from the signal and utilizing an imaging algorithm, such as a tomographic algorithm, to construct an image of the damage in the structure. Sensors may be permanently mounted. Imaging may be performed by comparing data at points in time to original data or without baseline data. Numerical algorithms may be used to extract features from the waveforms. Parallel shear polarization elements, polled through 760, may be pulsed through the thickness of the element as a non-limiting example.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A method of a non-destructive examination of a piece of material, comprising:
   producing a guided wave into a piece of material to be examined from at least two transducers disposed in a phased array on an angle beam wedge, wherein the guided wave is placed into the material through a synthetically changed incident angle;
   receiving the guided wave from the piece of material; and
   determining one of a presence of defects and lack of defects in the piece of material from the received guided wave.

2. The method according to claim 1, further comprising:
   controlling a mode of the produced guided wave by changing a time delay schedule across the array followed by changing an excitation frequency after producing the guided wave in the piece of material.

3. A method of performing a non-destructive examination of a piece of material, comprising:
   producing a guided wave in a material from a transmitter including a piezoelectric sensor disposed within a first guided wave wheel disposed on the material;
   controlling a mode of the guided wave by changing an incident angle and a frequency of the piezoelectric sensor disposed within the first guided wave wheel probe;
   receiving the guided wave in the material at a receiver; and
   determining a presence of defects in the material from the received guided wave.

4. The method according to claim 3, wherein the transmitter and receiver are disposed within the first guided wave wheel.

5. A non-destructive examination sensor, comprising:
   a housing including a first surface configured to be disposed on a surface of a material; and
   a piezo element placed at least partially within the housing, wherein the piezo element includes a frustum of a cone for producing a guided wave having a frequency based on a width of the piezo element and an angle between an outer surface of the piezo element and an axis perpendicular to the first surface of the housing.

6. The non-destructive examination sensor according to claim 5, wherein the housing is made of a polymer or metallic material.

7. The non-destructive examination sensor according to claim 5, wherein the piezo element is segmented.

8. A method of performing a non-destructive examination of a piece of material, comprising:
   exciting a non-destructive examination the-sensor at an angle between 0° and 360° over the piece of material to produce a guided wave in the piece of material, the non-destructive examination sensor including
      a polymer or metallic housing having a surface disposed on a surface of the material, and
      a piezo element disposed at least partially within the housing, the piezo element including a frustum of a cone for producing a guided wave having a frequency based on a width of the piezo element and an angle between an outer surface of the piezo element and an axis perpendicular to the surface of the housing;
   receiving the guided wave from the piece of material; and
   determining a presence of defects in the material from the received guided waves.

9. The method according to claim 8, wherein the sensor is segmented.

10. The method according to claim 8, wherein a frequency is changed during the producing of the guided wave in the material.

11. A method for analysis of health of a structure, comprising:
    producing a guided wave into the structure to be examined from at least one shear horizontal sensor disposed on the structure, wherein the guided wave is placed into the structure to cause at least one shear motion in the structure;
    receiving the guided wave from the structure; and
    determining the health of the structure from one of a presence of defects and lack of defects in the structure from the received guided wave.

12. The method according to claim 3, wherein the receiver is disposed within a second guided wave wheel.

* * * * *